though-holes
United States Patent [19]

Heywang-Koebrunner

[11] Patent Number: 5,681,327
[45] Date of Patent: Oct. 28, 1997

[54] STEREOTACTIC AUXILIARY MEANS FOR TOMOGRAM-GUIDED IMPLEMENTATION OF A BIOPSY

[75] Inventor: Sylvia Heywang-Koebrunner, Engelsdorf, Germany

[73] Assignee: Siemens Aktiengesellschaft, Munich, Germany

[21] Appl. No.: 564,638

[22] Filed: Nov. 29, 1995

[30] Foreign Application Priority Data

Nov. 30, 1994 [DE] Germany .......... 44 42 608.9

[51] Int. Cl.$^6$ .......... A61B 19/00
[52] U.S. Cl. .......... 606/130; 33/32.1; 128/653.1; 606/189
[58] Field of Search .......... 606/130, 129, 606/189; 128/653.1, 665; 33/32.1, 32.3, 34, 35, 41.1, 41.4, 45

[56] References Cited

U.S. PATENT DOCUMENTS

| 4,370,811 | 2/1983 | Triggs et al. .......... 33/32.1 |
| 4,535,782 | 8/1985 | Zoltan .......... 128/665 |
| 4,580,561 | 4/1986 | Williamson .......... 606/130 |
| 4,875,478 | 10/1989 | Chen .......... 128/653.1 |
| 4,930,143 | 5/1990 | Lundgren et al. .......... 128/653.1 |
| 5,056,523 | 10/1991 | Hotchkiss, Jr. et al. .......... 606/130 |
| 5,437,280 | 8/1995 | Hussman .......... 128/653.2 |
| 5,534,778 | 7/1996 | Loos et al. .......... 606/130 |

FOREIGN PATENT DOCUMENTS

| 1206116 | 12/1965 | German Dem. Rep. .......... 606/130 |
| 43 25 206 | 2/1994 | Germany . |

OTHER PUBLICATIONS

"A Device For Precision Needle Biopsy Of The Breast At Mammography," Mühlow, The American Journal of Roentgenology, vol. 21, No. 4, 1974, pp. 843–845.

Primary Examiner—Sam Rimell
Assistant Examiner—Justin R. Yu
Attorney, Agent, or Firm—Hill, Steadman & Simpson

[57] ABSTRACT

A stereotactic auxiliary attachment for a tomography apparatus for conducting a tomogram-guided biopsy of an examination subject has two compression plates for fixing the examination subject therebetween, with through-holes arranged in each compression plate enabling a guided access of a biopsy needle. An optical marking system is provided which optically marks the through bore most suitable inserting and guiding the biopsy needle for the biopsy, after the location of the lesion has been identified in a tomogram.

4 Claims, 2 Drawing Sheets

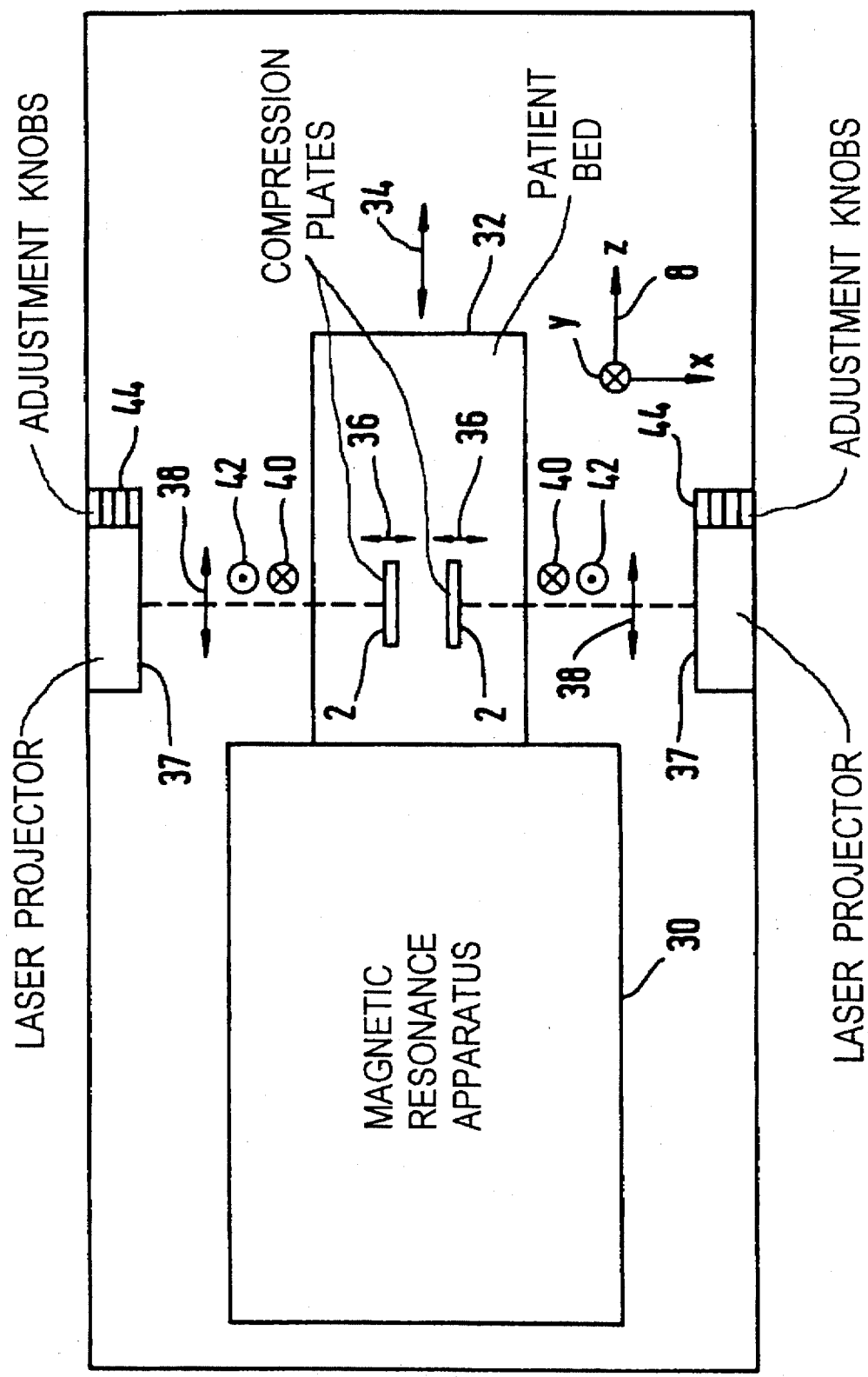

STEREOTACTIC AUXILIARY MEANS FOR TOMOGRAM-GUIDED IMPLEMENTATION OF A BIOPSY

BACKGROUND OF THE INVENTION

1. Field of the Invention

The invention is directed to a stereotactic auxiliary attachment for a tomography apparatus for conducting a tomogram-guided biopsy of an examination subject.

2. Description of the Prior Art

German OS 43 25 206 discloses a stereotactic auxiliary attachment having two compression plates for fixing the examination subject therebetween, marking means connected to the compression plates that generates visible marks in a tomogram, and through-holes in the compression plates and that enable a guided access of a biopsy needle. The stereotactic auxiliary attachment disclosed therein is fashioned for the implementation of a biopsy of a female breast with the assistance of magnetic resonance tomograms. The marker means connected to at least one compression plate generates marks in the tomogram that enable an exact allocation of the lesion visible in the tomogram to the actual position in the stereotactic auxiliary attachment. After measuring the position in the tomogram, the most favorable access hole in the compression plate for a biopsy needle must be selected. This can ensue, for example, by counting the through-holes arranged in a grid until the most favorable one is reached. The risk of a miscount exists particularly in the case of a large number of through-holes. Control counts can reduce this risk. In general, however, this method is complicated and subject to error.

The article by Anders Mühlow, "A Device for Precision Needle Biopsy of the Breast at Mammography", that appeared in *The American Journal of Roentgenology*, Vol. 121, No. 4, 1974, pp.843–845, discloses a stereotactic auxiliary attachment for X-ray mammography wherein through-holes arranged in the compression plate are identified by engraved letters and numerals. The through-holes together with the letters and numerals are imaged on a fluoroscopic image, so that through-holes suitable for the biopsy can be identified in the fluoroscopic image. This apparatus, however, is not suitable for tomogram-guided biopsy because neither the through-holes nor the coordinates belonging thereto are visible in the tomogram.

SUMMARY OF THE INVENTION

It is an object of the present invention to provide a stereotactic auxiliary attachment that enables a reliable selection of an optimum through hole for the implementation of the biopsy.

This object is achieved in a stereotactic auxiliary attachment having means for optically marking through-holes, the means for optically marking being formed by movable marks that can identify through-holes suitable for the biopsy with reference to the lesion-locating marker means. After the means for optically marking are set, the optimum through hole for the biopsy needle can then be used with high reliability.

In one embodiment the means for optically marking includes two coordinate marks residing perpendicularly on one another and which are adjustable independently of one another. The expanse (area) of the lesion that can be acquired in a projection can thus be set on the compression plate.

In another embodiment a light-beam localizer is provided as the means for optically marking for generating light marks on at least one compression plate, the light-beam localizer having adjustment means with which the position of the light marks on the compression plate can be varied. No physical marks that could impede the attending person during the implementation of the biopsy are thus present in the proximity of the optimum through hole.

DESCRIPTION OF THE DRAWINGS

FIG. 2 is a side view of a second embodiment of a stereotactic auxiliary attachment constructed in accordance with the principles of the present invention wherein light-beam localizer is used for generating a light mark.

DESCRIPTION OF THE PREFERRED EMBODIMENT

Figure 1:
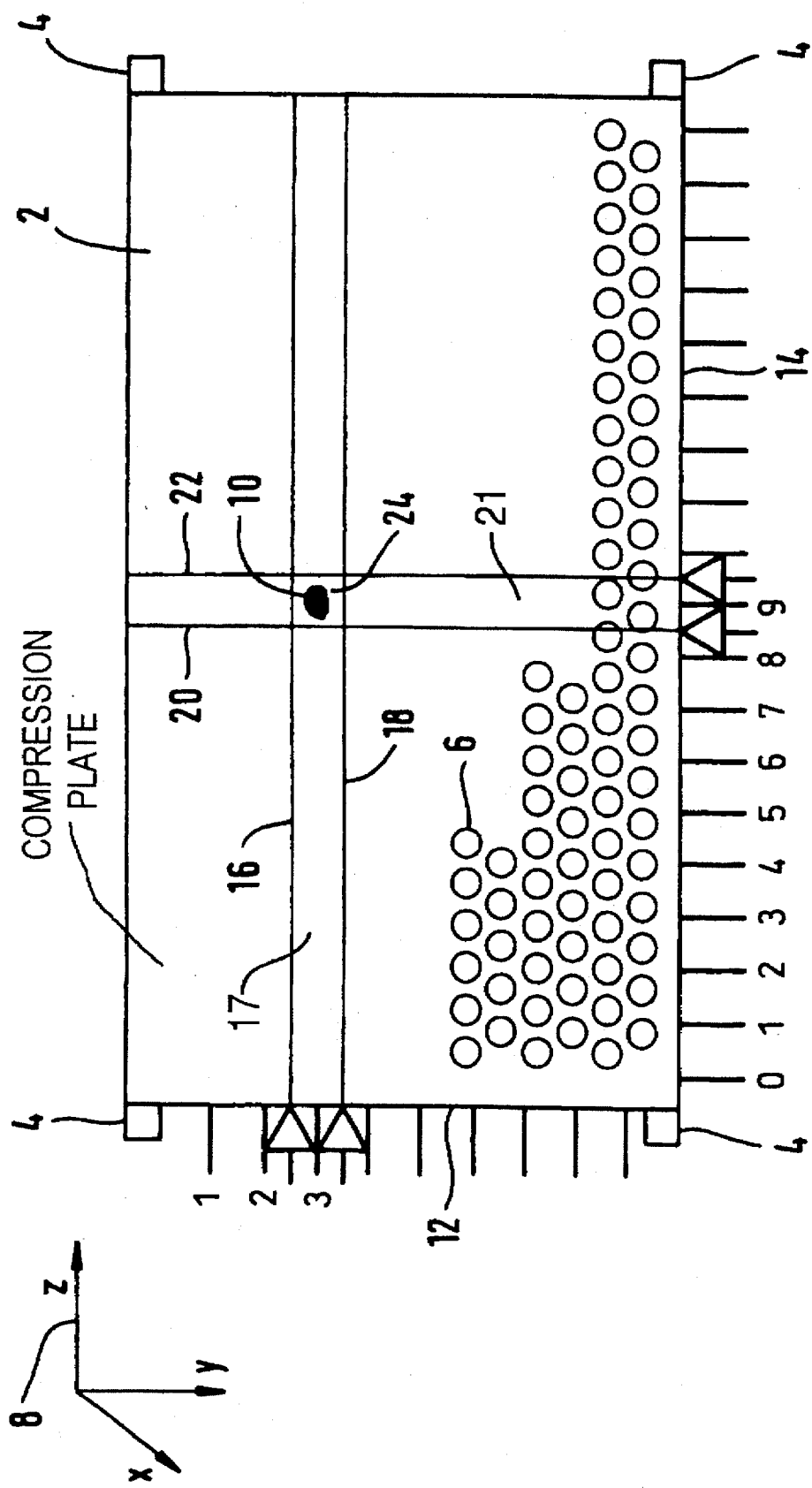
FIG. 1 is a plan view of a first embodiment of a stereotactic auxiliary attachment constructed in accordance with the principles of the present invention wherein an optical marking ensues using displaceable marks.

In a plan view, FIG. 1 shows a compression plate 2. An examination subject such as, for example, a female breast, is fixed between two such compression plates 2 in order to produce tomograms by means of, for example, magnetic resonance tomography and in order to subsequently implement a biopsy, as disclosed in German OS 43 25 206. To that end, a marker system 4 that generates marks visible in the tomogram is located at both compression plates 2.

Through-holes 6 are introduced into the compression plates 2 in a regular grid, a guided access of a biopsy needle to the examination subject being possible via these holes.

A Cartesian coordinate system whose origin is located, for example, at the upper left part of the marker system 4 shall be referenced for further explanation of FIG. 1. The coordinate system 8 is shown next to the left upper part of the marker system 4 in FIG. 1 only for greater clarity. The y-z-plane is located in the plane of the drawing, whereas the x-axis is directed upwardly out of the plane of the drawing. With reference to the coordinate system 8, the compression plate 2 is aligned parallel to the y-z-plane. The position of a lesion 10 visible in the tomogram, from which a tissue sample is then to be taken with a biopsy needle, is measured with the assistance of marks generated by the marker system 4 that are likewise visible in the tomogram. Values for the y-coordinate and the z-coordinate result from the measuring event. The depth position of the lesion 10 and, thus, the paracentesis depth of the biopsy needle is derived from the position of the tomogram in which the lesion 10 is visible. Here, the coordinate values of the maximum outside dimensions of the lesion are measured, so that two values are known both for the y-coordinate and for the z-coordinate. The area of the lesion 10 is thus acquired as a projection onto the y-z-plane.

A vertical scale and two displaceable marks 16 and 18 and, are located at the left side 12 of the compression plate 2. A horizontal scale and two displaceable marks 20 and 22 are located at the lower side 14 of the congression plate 2. The marks 16,18 and 20,22 are shown as lines and each pair of marks respectively represents the edges of thin, ruler-like carries 17 and 21. A region 24 circumscribed by the marks, that is rectangular, marks the access region of the biopsy needle to the lesion 10. The attending person then selects that through hole 6 that seems most favorable for the implementation of the biopsy.

The embodiment shown in FIG. 2 generates a light mark corresponding to what is shown in FIG. 1. The tomogram apparatus, a magnetic resonance apparatus 30 in this case, has a displaceable patient bed 32 with which the patient can be inserted into the examination space of the magnetic resonance apparatus 30. The displaceability of the patient bed 32 into and out of the examination space of the magnetic resonance apparatus 20 is symbolized by a double arrow 34.

For examination of the female breast, a patient (not shown) is situated in a prone position on the patient bed 32, and the breast to be examined is fixed by two compression plates 2 like those described on the basis of FIG. 1. The compression plates 2 are arranged so as to be displaceable toward and away from one another, this being symbolized by double arrows 36. A light-beam, for example a laser projector 37, is located at each of two opposite walls at the level of the compression plates. Each projector 37 generates line-shaped light marks at those sides of the compression plates 2 facing away from the examination subject. Each light mark comprises two coordinate, marks for the y-z-coordinate the light marks residing perpendicularly on one another and having adjustable independently of one another by means of the projectors 37, as was already set forth with reference to FIG. 1. The displaceability of the coordinate marks in the z-direction is illustrated with a double arrow 38, whereas the displaceability of the marks in the y-direction is shown with a symbolic arrow shaft 40 and a symbolic arrowhead 42.

For setting the respective coordinate marks of two light marks, four adjustment knobs 44 for independently setting the individual coordinate marks provides at each projector 37. After the registration of tomograms of the breast, with the patient bed 32 with the patient thereon introduced into the examination space of the magnetic resonance apparatus 30, the tomograms are interpreted and the position of a lesion 10 is measured in the tomogram in the manner set forth above. During this time, the patient bed 32 is moved out of the examination space. After a zeroing of the light marks on the compression plate 2 with respect to the marker system 4, the position of the light marks 16,18,20 and 22 can be set to the lesion 10 to be examined, using the adjustment knobs 44.

Although modifications and changes may be suggested by those skilled in the art, it is the intention of the inventor to embody within the patent warranted hereon all changes and modifications as reasonably and properly come within the scope of her contribution to the art.

I claim as my invention:

1. A stereotactic auxiliary attachment for a tomography apparatus for conducting a tomogram-guided biopsy of an examination subject, said stereotactic auxiliary attachment comprising:

two compression plates for fixing an examination subject therebetween, each compression plate having a plurality of through-holes therein adapted for receiving a biopsy needle therethrough;

lesion marking means connected to said compression plates for generating a visible mark in a tomogram identifying a location of a lesion in said examination subject relative to said visible mark; and relative to said lesion marking means, a selected means for two-dimensionally optically markings through-hole of said plurality of through-holes in one of said compression plates, after identification of the location of the lesion relative to said visible mark, best positioned for guiding a biopsy needle to said lesion.

2. A stereotactic auxiliary attachment as claimed in claim 1 wherein said means for optically marking comprises first and second pairs of coordinate marks, said first and second pairs of coordinate marks being disposed and movable along respective first and second directions oriented perpendicularly relative to each other, and means for adjusting said first and second pairs of coordinate marks respectively along said first and second directions independently of each other.

3. A stereotactic auxiliary attachment as claimed in claim 2 wherein said means for adjusting comprises a first carrier movable along said first direction and a second carrier movable along said second direction, and wherein said first pair of coordinate marks comprises two parallel line marks on said first carrier and said second pair of coordinate marks comprises two parallel line marks on said second carrier.

4. A stereotactic auxiliary attachment as claimed in claim 2 wherein said means for optically marking comprises a first light beam projector for generating a first pair of parallel light beams and a second light beam projector for generating a second pair of parallel light beams, said first and second pairs of parallel light beams respectively forming said first and second pairs of coordinate marks, on at least one of said compression plate, and wherein said means for adjusting comprises means for adjusting a position of each of said first pair of parallel light a position of said first direction and means for adjusting a position of said second pair of parallel light beams along said second direction.

* * * * *